United States Patent
Steiner et al.

(10) Patent No.: US 6,669,902 B1
(45) Date of Patent: Dec. 30, 2003

(54) OZONATED FOAM MEDIUM AND PRODUCTION SYSTEM AND METHOD FOR SANITIZING A FOOD PROCESSING ENVIRONMENT

(75) Inventors: Edward F. Steiner, Lombard, IL (US); James T. C. Yuan, Naperville, IL (US)

(73) Assignees: L'Air Liquide - Societe Anonyme a'Directoire et Conseil de Surveillance pour l'Etude et l'Exploitation des Procedes Georges Claude, Paris (FR); American Air Liquide, Fremont, CA (US)

( * ) Notice: Subject to any disclaimer, the term of this patent is extended or adjusted under 35 U.S.C. 154(b) by 132 days.

(21) Appl. No.: 09/708,859

(22) Filed: Nov. 8, 2000

(51) Int. Cl.$^7$ ................................................. A61L 2/16
(52) U.S. Cl. ............................. 422/28; 261/DIG. 26; 422/1; 422/29; 510/108
(58) Field of Search .......................... 422/1, 28, 29, 422/186.07; 261/DIG. 26; 252/307, 103; 210/632, 748; 510/108

(56) References Cited

U.S. PATENT DOCUMENTS

| | | | | |
|---|---|---|---|---|
| 4,136,027 A | * | 1/1979 | Sakamoto et al. | 210/63 Z |
| 4,584,002 A | * | 4/1986 | Cox et al. | 55/257 |
| 5,302,298 A | * | 4/1994 | Leitzke | 210/748 |
| 5,484,549 A | * | 1/1996 | Hei et al. | 252/103 |
| 6,042,089 A | * | 3/2000 | Klein | 261/76 |
| 6,066,348 A | | 5/2000 | Yuan et al. | |
| 6,076,229 A | | 6/2000 | Berglund | 15/321 |
| 6,086,833 A | | 7/2000 | Conners et al. | |
| 6,115,862 A | | 9/2000 | Cooper et al. | |
| 6,120,614 A | | 9/2000 | Damron et al. | |

FOREIGN PATENT DOCUMENTS

| | | |
|---|---|---|
| EP | 0 819 388 A1 | 1/1998 |
| FR | 0727243 A1 * | 8/1996 |
| WO | WO 98/00227 | 1/1998 |
| WO | WO 01/27986 A1 | 4/2001 |
| WO | WO 01/35755 A1 | 5/2001 |

OTHER PUBLICATIONS

"Biocidal Efficacy of Ozone in Processing," Reprinted from Fresh–Cut™ Magazine, Nov. 1998, 3 pages.

* cited by examiner

Primary Examiner—Robert J. Warden, Sr.
Assistant Examiner—Sean E. Conley
(74) Attorney, Agent, or Firm—Linda K. Russell; Chritopher J Cronin

(57) ABSTRACT

A method for sanitizing a food processing environment includes preparing an ozonated foam sanitizing medium and applying the sanitizing medium to either objects in the food processing environment, such as food processing equipment, food contact surfaces, interior surfaces of the food processing facility, or the ambient environment within the food processing facility, or both the objects within the food processing facility and the ambient environment of the food processing facility. An ozonated foam sanitizing medium includes a foaming agent dissolved in an aqueous solution and an ozone concentration of at least about 0.1 ppm and is prepared by either injecting gaseous ozone or introducing an aqueous ozone solution into an aqueous solution containing a foaming agent. In a system for generating the ozonated foam medium, the gaseous ozone can be injected with a feed gas, such as oxygen, air, an inert gas, and mixtures thereof. Additionally, an inert gas, such as nitrogen, carbon dioxide, argon, krypton, xenon, neon, and mixtures thereof can be injected separately into the aqueous foam solution. Once prepared, the ozonated foam is applied to a surface within the food-processing environment to a thickness of about 0.25 inches to about 7 inches or more, and allowed to stand for a predetermined period of time. The ozonated foam is then washed away with an aqueous solution.

20 Claims, 2 Drawing Sheets

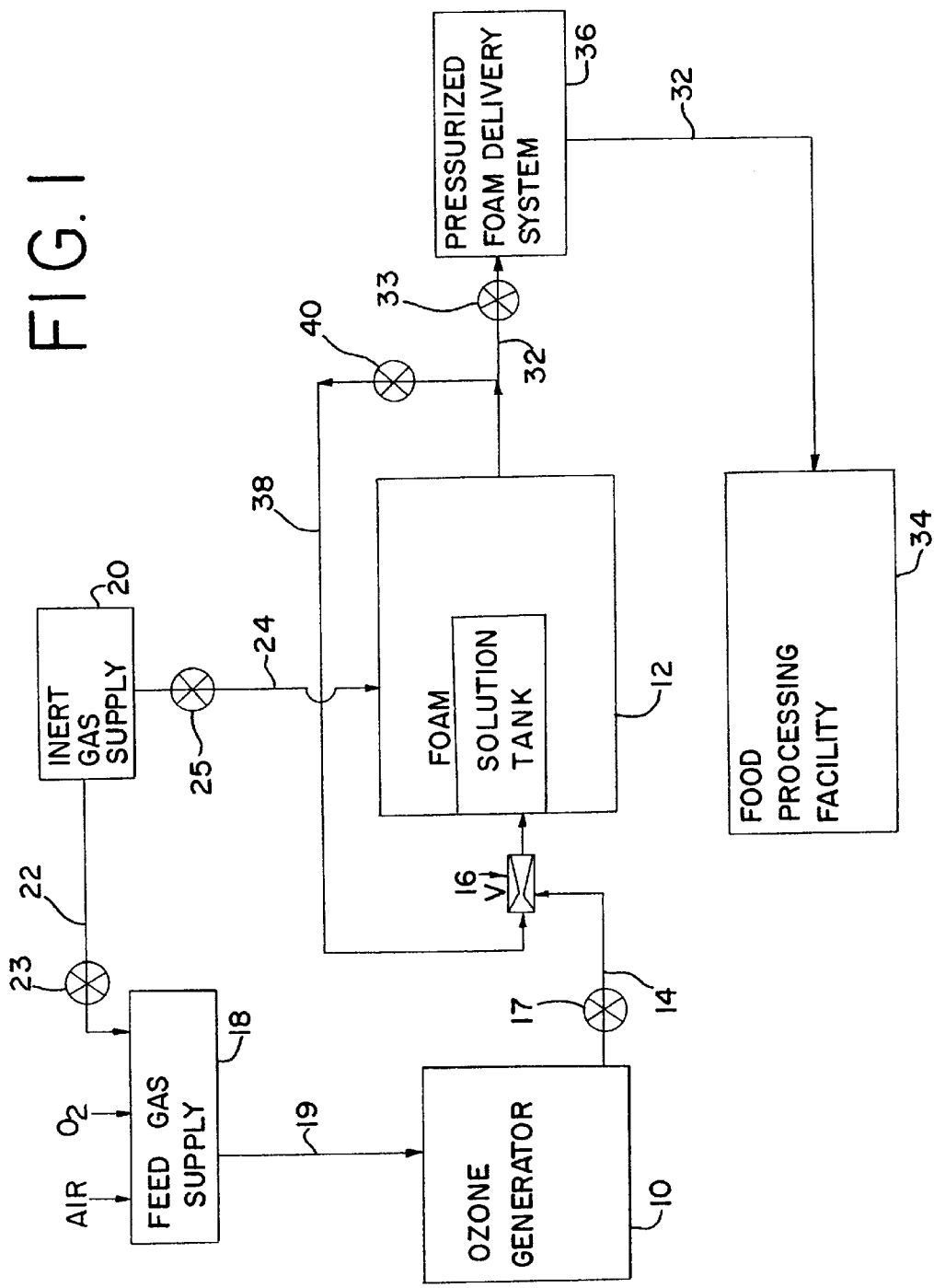

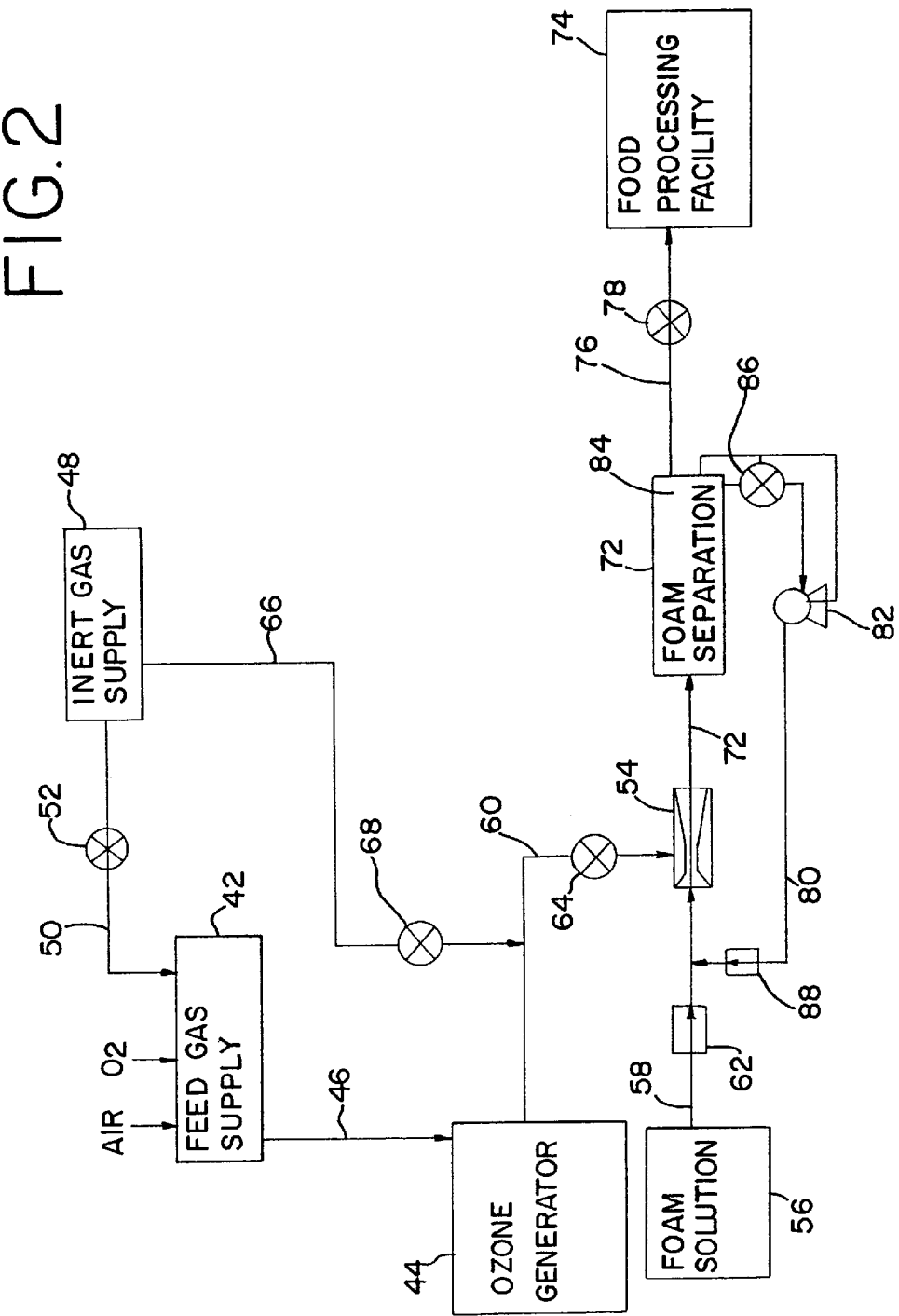

OZONATED FOAM MEDIUM AND PRODUCTION SYSTEM AND METHOD FOR SANITIZING A FOOD PROCESSING ENVIRONMENT

FIELD OF THE INVENTION

The present invention relates, generally, to sanitizing compounds and sanitization methods and, more particularly, to materials, methods and systems for sanitizing food processing equipment and facilities using ozone.

BACKGROUND OF THE INVENTION

Microbial outgrowth is a primary cause of food spoilage. The presence of pathogenic microorganisms on food products can potentially lead to food-borne outbreaks of disease and can cause significant and economic loss to food processors. Food products can become contaminated within a food-processing environment. For example, processing equipment, such as knives, mixers and the like, can provide favorable locations for the growth of pathogenic microorganisms. Additionally, food contact surfaces, such as cutting boards and conveyor belts, and the like can become contaminated and support the growth of microorganisms. Also, microorganisms can be transported through a food processing facility by entrainment in the ambient air circulated throughout the food processing facility. Once airborne, microorganisms can become attached to numerous surfaces within the food processing facility, such as ceilings, air ducts, wall surfaces, floors and the like. The need to delay the onset of spoilage and to eliminate pathogens has led the food processing industry to seek effective means for disinfecting food processing equipment and facilities.

Presently, food processors use heat or chemicals to sanitize their food processing facility. Heat, in the form of steam or hot water, is a commonly used method for disinfecting food and for cleaning floors, walls and food contact surfaces. However, the efficiency of steam or hot water is low on large, exposed surface areas. Additionally, steam or hot water can adversely affect food products by thermally degrading the food products and by breaking down nutrients from the food products.

Widely used chemical sanitizers include chlorine-based chemicals and quaternary ammonium compounds. The chemical agents are relatively effective against microorganisms and reasonably inexpensive to apply. However, each particular chemical has a corresponding specific range of activity with respect to the population of pathogenic microorganisms commonly found in a food-processing environment. Additionally, the effectiveness of many chemicals depends upon carefully maintaining storage conditions and solution characteristics. For example, chlorine is effective at a pH of about 6 to about 8, and becomes less effective outside of that pH range. However, chlorine can produce toxic by-products that are harmful to human health, such as chloramines and trihalomethanes.

Another widely used chemical agent is ozone ($O_3$). Ozone is a very strong oxidizing agent, having an oxidation potential more than 1.5 times that of chlorine, and approximately 1.2 times that of hydrogen peroxide. Ozone is normally produced by passing an oxygen-containing gas through ultraviolet light or a corona discharge. Ozone has been shown to be a highly reactive oxidant capable of destroying many cellular constituents in living cells. Further, an additional advantage of ozone relates to its natural decomposition into oxygen, an environmentally friendly gas. At low levels, ozone will decompose into oxygen within a few hours. Food processors have used gaseous ozone to disinfect foods stored in bulk storage containers, such as fruits and vegetables stored in warehouses. Additionally, processes have been developed using an ozone solution made by injecting ozone gas into water, which is then used to sanitize and disinfect food-processing surfaces.

Given that ozone decomposes into a non-toxic gas and that it will not impart odor or taint to food products, and leaves no residue after application, further development of ozone application technology is warranted. In particular, application technology is needed that maximizes the effectiveness of ozone's inherent capability to kill pathogenic microorganisms.

BRIEF SUMMARY

The present invention is for an ozonated foam medium and production system, and for a method of sanitizing a food-processing environment-using ozonated foam. In one embodiment of the invention, an ozonated foam-sanitizing medium is prepared. The sanitizing medium is then applied to objects in the food-processing environment, or the ambient of the food-processing environment, or both, to the objects and the environment. The ozonated foam-sanitizing medium can be applied by a variety of means, such as spraying, atomization and liquid application.

In one embodiment of the invention, the ozonated medium is prepared by injecting a gas comprising ozone into an aqueous solution containing a foaming agent. Further, the ozone can be injected with a feed gas, such as oxygen, air and mixtures of oxygen and air. Additionally, the feed gas can be an inert gas or a mixture of air and an inert gas. Other feed gas combinations are possible, such as a mixture of an inert gas and oxygen $O_2$, and a mixture of air and oxygen. The inert gas can be nitrogen ($N_2$), carbon dioxide ($CO_2$), argon (Ar), krypton (Kr), xenon (Xe), neon (Ne) and mixtures of these gases.

In another embodiment of the invention, an ozonated foam-sanitizing medium is prepared by injecting a gas comprising ozone into an aqueous solution containing a foaming agent, followed by injecting an inert gas directly into the sanitizing medium.

In yet another embodiment of the invention, an ozonated foam-sanitizing medium is prepared by mixing an aqueous ozone solution into an aqueous solution containing a foaming agent.

In a more particular embodiment of the invention, an ozonated foam-sanitizing medium is prepared with an initial ozone concentration, such that, after applying the ozonated foam-sanitizing medium, an ozone concentration of at least about 0.1% of the initial concentration is maintained up to about 30 minutes after applying the sanitizing medium. In accordance with the invention, the preparation of an ozonated foam functions to provide increased ozone concentration over extended periods of time following the application of the sanitizing foam. Thus, the ozone operates to kill pathogenic microorganisms over an extended period of time after its initial application.

In a still further embodiment of the invention, a foaming agent is mixed into an aqueous solution while maintaining the aqueous solution at a temperature of about 0° C. to about 70° C. A sanitizing medium is then formed by injecting a gas comprising ozone into the aqueous solution.

In a detailed aspect of the invention, ozonated foam is prepared by adding a surfactant to an aqueous solution and injecting ozone into the aqueous solution to form an initial ozone concentration of at least about 0.1 ppm. The ozonated foam is then sprayed on food contact surfaces of food processing equipment or facilities, and the ozonated foam is then allowed to stand on the food contact surfaces for a predetermined length of time. The ozonated foam is then washed away with an aqueous solution. By effectively confining ozone within a foam-sanitizing medium, the ozone can act on the food processing surfaces over a prolonged period of time. Also, by exposing pathogenic microorganisms to relatively high concentrations of ozone for a relatively long duration, the effectiveness at killing microorganisms can be increased. Additionally, the ozone can be recycled from the aqueous solution used to wash away the ozonated foam after it has completed a sanitization cycle.

A system for producing an ozonated foam medium includes an injector coupled to either a foam solution tank or to a foam separator. An ozone generator receives feed gas from a feed gas supply and produces a gas comprising ozone and transfers the gas comprising ozone to the injector. Both batch processing and continuous processing systems produce an ozonated foam medium for use in a food-processing facility.

BRIEF DESCRIPTION OF THE DRAWING

FIG. 1 is a schematic diagram of an exemplary batch processing, ozonated foam generation and delivery system arranged in accordance with the invention; and FIG. 2 is a schematic diagram of an exemplary continuous processing, ozonated foam generation and delivery system arranged in accordance with the invention.

DETAILED DESCRIPTION OF THE PREFERRED EMBODIMENTS

The present invention is for ozonated foam and a method for sanitizing a food-processing environment using ozonated foam. Ozonated foam is particularly effective at sanitizing food processing equipment and food contact surfaces, food surfaces, as well as the ambient atmosphere within a food processing facility. The application of ozone to kill pathogenic microorganisms is particularly effective when delivered in a foam-sanitizing medium. The foam medium retains ozone at a relatively high concentration level for a prolonged period of time. By maintaining high concentrations of ozone, more pathogenic bacteria can be killed with each application of the foam media. Additionally, the prolonged exposure to the high ozone concentration level provided by the foam media also increases the number of pathogenic microorganisms killed by the ozone. As used herein, the term "sanitize," and variations and derivation thereof, means the reduction of the microbial population of surfaces contacted by ozonated foam.

In one embodiment of the invention, ozonated foam is applied directly to processing equipment, such as knives, mixers, blenders and the like. Additionally, the ozonated foam can be applied to food contact surfaces within a processing facility, such as cutting boards, conveyor belts, food storage containers, food freezers and the like. Cryogenic freezing methods are known in the art that use a mixture of liquid nitrogen and liquid oxygen in amounts approximating the composition of atmospheric air to freeze food products. For example, commonly-assigned U.S. Pat. No. 5,921,091 to Foss, et al. describes the use of liquid nitrogen and oxygen mixtures in freezers, such as tunnel freezers, spiral freezers, and immersion freezers and is incorporated by reference herein. The ozonated foam of the present invention can be applied to sanitize cryogenic freezing equipment.

Further, the ozonated foam can be applied to interior surfaces of a food processing facility, such as floors, drains, walls, ceilings and the like. Also, the ozonated foam can be used to sanitize the ambient air within a food processing facility. For example, the ozonated foam can be applied to inner surfaces of air circulation systems and the like. In conjunction with the application of ozonated foam to food contact surfaces and the like, the ozonated foam can also be applied directly to the food products during processing within a food processing facility.

In one embodiment of the invention, ozonated foam is prepared by introducing a foaming agent to an aqueous solution. A gas comprising ozone is then injected into the aqueous solution. A feed gas can be introduced into an ozone generator to generate an ozone gas stream. The feed gas can be $O_2$, air or a mixture of $O_2$ and air. Additionally, the feed gas can be a mixture of $O_2$ and air and a mixture of $O_2$ and an inert gas, such as $N_2$, $CO_2$, Ar, Kr, Xe and Ne. In an alternative embodiment, the foregoing inert gases can be injected separately into the aqueous solution. The injection of feed gas and inert gas can create a certain degree of turbulence, which can increase the foaming action during the ozonated foam generation process.

FIG. 1 is a schematic diagram of an exemplary batch processing, ozonated foam generation and delivery system arranged in accordance with one embodiment of the invention. Those skilled in the art will recognize that the exemplary system illustrated in FIG. 1 is merely an example of a variety of arrangements for the generation and delivery of ozonated foam. For purposes of illustration, only the major components of the exemplary system are shown in FIG. 1.

An ozone generator 10 is coupled to a foam solution tank 12 by an ozone delivery line 14 and an ozone injector 16. In ozone generator 10, ozone is preferably generated from, a feed gas of $O_2$ or air, and "ozone gas" is typically a gas comprising at least about 0.1% by weight ozone and a balance of $O_2$ or a mixture of $O_2$ and an inert gas, such as $N_2$. A metering valve 17 regulates the flow of gas from ozone generator 10 to injector 16. A feed gas supply 18 is coupled to ozone generator 10 by a feed gas line 19. An inert gas supply 20 is coupled to feed gas supply 18 through a first inert gas line 22 equipped with a metering valve 23. Feed gas supply 18 is also serviced by an air supply and an oxygen supply. Inert gas supply 20 is also coupled to foam solution tank 12 through a second inert gas line 24 equipped with a metering valve 25. Ozone and feed gas are injected into foam solution tank 12 by ozone injector 16. In a preferred embodiment, ozone injector 16 includes a venturi-type injector, in which the pressure of the ozone and feed gas is reduced as the gas passes through ozone injector 16. Alternatively, ozone injector 16 can include a porous sintered-metal sparger, and the like.

Those skilled in the art will appreciate that other ozone generation and delivery systems are possible. For example, systems are known in the art in which ozone gas is generated using a vacuum pressure ozone gas generator. Additionally, ozone generators operating at a low pressure, and generating a low volume of ozone gas for delivery to a fluid injector are also known in the art. The fluid injector receives a high-pressure carrier fluid from a carrier fluid source, such as feed gas supply 18, and causes the ozone to be entrained in a stream of carrier fluid. Such a system is described in commonly-assigned U.S. Pat. No. 6,086,833, which is incorporated by reference herein. Ozone is entrained in the carrier fluid by passing the carrier fluid through a venturi diffuser inside the injector. This creates a negative pressure in the ozone line, thus drawing the ozone into the carrier fluid and creating a highly homogenized fluid jet. Additionally, the ozone/carrier fluid jet may also be selectively humidified before injection into foam solution tank 12.

Regardless of the particular ozone generation equipment that is used, the injection of a gas comprising ozone into foam solution tank 12 creates ozonated foam within foam solution tank 12. The ozonated foam is transported through a delivery line 32 into a food processing facility 34 by a pressurized foam delivery system 36. Delivery line 32 is equipped with a metering valve 33 and is also connected to a return line 38. Any liquid portion of the ozonated foam can be returned to foam solution tank 12 through return line 38, where metering valve 40 regulates the return flow.

In a preferred embodiment of the invention, an aqueous foaming agent solution is prepared by mixing a foaming agent into water in solution tank 12. The foaming agent can be any of a number of substances that are capable of forming a foam media. For example, the foaming agent can be a surfactant, such as a surfactant available under the trade name "Polysorbate 20" from Seppic of Paris, France. Alternatively, the foaming agent can be a detergent, such as that found in human hair shampoo. Preferably, the aqueous solution is formed to have a concentration of foaming agent of about 0.01 to about 100% by weight.

After adding the foaming agent, ozone is added to the solution by, preferably, injecting a gas comprising ozone into the solution through ozone delivery line 14. The ozone gas stream is preferably injected with a feed gas from feed gas supply 18 to form an initial ozone concentration of at least about 0.1 ppm in foam solution tank 12.

In an alternative embodiment, ozone is introduced by adding an aqueous ozone solution to the aqueous solution containing the foaming agent. Preferably, an aqueous solution having an ozone concentration of about 0.1 ppm to about 10 ppm is mixed with the foaming agent solution to form ozonated foam.

In accordance with the invention, inert gases from inert gas supply 20 may be injected into the aqueous foam solution in foam solution tank 12. The inert gas can be injected either together with the injection of gaseous ozone through ozone delivery line 14 or, alternatively, injected separately through second inert gas line 24 into the aqueous foam solution in foam solution tank 12. Preferably, an inert gas, such as $N_2$, $CO_2$, Ar, Kr, Xe or Ne mixed with either oxygen or air is injected into the aqueous foam solution. Further, a mixture of the foregoing inert gases with either air or oxygen can be injected into the aqueous foam solution.

Preferably, the foam solution in foam solution tank 12 is maintained at a temperature of about 0° C. to about 35° C. and, more preferably, about 4° C., while injecting gaseous ozone or introducing an aqueous ozone solution. The ozone foam production efficiency is enhanced by temperature control and by the turbulence created by the injection of inert gas.

FIG. 2 is a schematic diagram of an exemplary continuous processing, ozonated foam generation and delivery system arranged in accordance with the invention. In similarity with the batch system illustrated in FIG. 1, the continuous processing system includes a feed gas supply 42 coupled to an ozone generator 44 by a feed gas line 46. Feed gas supply 42 is also coupled to an inert gas supply 48 by an inert gas line 50 equipped with a metering valve 52. Feed gas supply 42 is also serviced by an air supply and an oxygen supply.

An injector 54 receives a stream of aqueous foam solution from a foam solution supply 56 through a foam solution line 58, and receives a gas comprising ozone from ozone generator 44 through ozone line 60. Preferably, injector 54 includes a venturi valve that reduces the pressure and increases the velocity of the aqueous foam solution. As in the previous embodiment, other types of injectors are also contemplated, such as a sparger and the like. A check valve 62 prevents the back flow of foam solution in solution line 58 and a metering valve 64 regulates the flow of ozone into injector 54. Inert gas from inert gas supply 48 can be introduced to the flow of ozone from ozone generator 44 through an inert gas line 66. A control valve 68 regulates the flow of inert gas through inert gas line 66.

Injector 54 feeds an aqueous stream of ozonated foam solution to a foam separator 70 through a feed line 72. Foam separator 70, operating at a lower pressure than injector 54, separates the ozonated foam medium from the liquid component of the ozonated foam solution and outputs a stream of foam medium to a food processing facility 74 through a foam delivery line 76. A metering valve 78 regulates the flow of ozonated foam medium through foam delivery line 76. A liquid return line 80 is connected to foam separator 70 and returns the liquid portion of the ozonated foam in foam separator 70 to foam solution line 58. Since the pressure within foam separator 70 is below that of injector 54, a pump 82 is provided in return line 80 to increase the pressure of the return liquid to facilitate the flow of liquid into foam solution line 58.

In accordance with one embodiment of the invention, a liquid level switch 84 is mounted in foam separator 70 and determines the liquid foam solution height of foam separator 70. When the foam solution height reaches a predetermined level, liquid level switch 84 activates pump 82 and a control valve 86 located in solution return line 80. A check valve 88 prevents the back flow of foam solution in solution return line 80.

In a preferred embodiment of the invention, solution line 58, injector 54, feed line 72, foam separator 70 and foam delivery line 76 are simply different sections of a single, elongated pipe. The diameter of the pipe varies along the longitudinal axis of the pipe to effectively change the solution pressure within the pipe. For example, the section containing injector 54 has a smaller diameter than the section containing foam separator 70. Those skilled in the art will recognize that the pressure will be lower in the foam separator section as a result of constant flow rate through a larger diameter section of the pipe. To increase the pressure of the foam medium, the diameter of the section containing foam delivery line 76 is smaller than the diameter of the section containing foam separator 70. Accordingly, the continuous production of ozonated foam medium can be realized through a relatively simple pipe design.

Those skilled in the art will recognize that the exemplary system illustrated in FIG. 2 is merely an example of a variety of arrangements for the generation and continuous delivery of ozonated foam. For purposes of illustration, only the major components of the exemplary system have been shown in FIG. 2.

Regardless of the particular system design used to generate the ozonated foam medium, once at the point of use, the ozonated foam can be applied to a thickness of from about 0.25 inches to as much as about 7 inches or more on a surface within a food processing facility. The ozonated foam can be applied by one of several methods, such as spraying, misting, atomization and the like. Preferably, the ozonated foam is allowed to stand on the surface to be sanitized for a period of time of about 2 to about 90 minutes.

After applying the ozonated foam, an ozone concentration of preferably at least about 0.1% of the initial concentration is maintained up to about 30 minutes after applying the sanitizing medium. In a more preferred embodiment, at least about 10% of the initial ozone concentration is maintained up to about 30 minutes, and in a most preferred embodiment, at least about 50% of the initial ozone concentration is maintained up to about 30 minutes.

After allowing the ozonated foam to stand on the surface to be sanitized for a predetermined period of time, the ozonated foam can be washed off the surface using an aqueous solution. The aqueous wash solution can be recycled to recover ozone remaining in the solution after the sanitization process. Alternatively, the wash solution can be discarded.

Without further elaboration, it is believed that one skilled in the art can, using the preceding description, utilize the invention to its fullest extent. The following preferred specific embodiment is, therefore, to be construed as merely illustrative of the invention and not to limit the remainder of the disclosure in any way whatsoever.

EXAMPLE

The following experiment was conducted to illustrate the benefits of applying ozone in a foam-sanitizing medium to a surface to be sanitized.

About 300 liters of water was chilled to a temperature of about 4° C. Then, the surfactant "Polysorbate 20" was added to form a surfactant concentration of about 0.5% by weight. Next, a gas mixture containing ozone and $O_2$ and having an ozone concentration of about 3 to about 4% by weight was injected at a rate of about 0.4 cubic meters per minute using a venturi-type injector to create ozonated foam. The ozone concentration in the foam was measured using the DPD colorimetric method (4500-Cl g.), as described in "Standard Methods for the Examination of Water and Wastewater," $19^{th}$ Ed., American Public Health Association, 1995.

After preparing the ozonated foam, ozone concentration measurements were periodically taken to determine the rate of ozone depletion within the ozonated foam. The results of the ozone concentration measurements are shown in the Table below.

TABLE

Ozone Concentration in Ozonated Foam

| Ozone Concentration (ppm) | Time (min) |
| --- | --- |
| 1.75 | 0 |
| 1.5 | 20 |
| .30 | 120 |

The data indicates that a relatively high ozone concentration can be maintained within the foam for a relatively long period of time. To perform the ozone concentration measurements, samples of the ozonated foam were withdrawn immediately after creating the foam, and at the time intervals shown in the Table. Importantly, gaseous ozone trapped within the foam continued to evolve after removing the samples from the ozonated foam. The gaseous ozone was observed to evolve from the foam for a period of about 15 minutes after removing each sample, as indicated by a darkening color within each foam sample.

Thus, it is apparent that there has been described in accordance with the invention, an ozonated foam medium and system and method for sanitizing a food processing environment using ozonated foam. While the invention has been described with reference to preferred embodiments thereof, it is to be understood that variations and modifications can be made by those skilled in the art without departing from the scope of the invention. For example, various types of applicators can be used to distribute the ozonated foam within a food processing facility. Accordingly, all such variations and modifications are within the scope of the present invention, as set forth in the appended claims and equivalents thereof.

What is claimed is:

1. A method for sanitizing a food processing environment comprising:

preparing an ozonated foam sanitizing medium having an initial ozone concentration; and applying the sanitizing medium to one of objects in the food processing environment, an ambient of the food processing environment and both the object and the ambient, wherein at least about 0.1 % of an initial ozone concentration is maintained up to about 30 minutes after applying the sanitizing medium.

2. The method of claim 1 further comprising washing away the sanitizing medium with an aqueous solution.

3. The method of claim 1, wherein applying the sanitizing medium comprises spraying the ozonated foam.

4. The method of claim 1, wherein the initial ozone concentration is at least about 0.1 ppm.

5. The method of claim 1, wherein preparing ozone comprises:

mixing a foaming agent into the aqueous solution; and injecting a gas comprising ozone into the aqueous solution.

6. The method of claim 1, wherein preparing ozone comprises:

mixing a foaming agent with an aqueous ozone solution; and injecting the ozone solution with a feed gas selected from the group consisting of oxygen, air and mixtures thereof, a mixture of air and an inert gas, a mixture of an inert gas and oxygen, and a mixture of air oxygen and an inert gas.

7. The method of claim 6, wherein the inert gas is selected from the group consisting of nitrogen, carbon dioxide, argon, krypton, xenon, neon, and mixtures thereof.

8. A method for sanitizing a food processing environment comprising:

preparing an ozonated foam sanitizing medium; and applying the sanitizing medium to one of objects in the food-processing environment, an ambient of the food processing environment and both the objects and the ambient, wherein preparing an ozonated foam sanitizing medium comprises providing an aqueous ozone solution containing a foaming agent and injecting a gas comprising ozone into the aqueous ozone solution.

9. The method of claim 8, wherein injecting a gas comprising ozone comprises injecting ozone with a feed gas selected from the group consisting of oxygen, air and mixtures thereof, an inert gas, a mixture of air and an inert gas, a mixture of an inert gas and oxygen, and a mixture of air oxygen and an inert gas.

10. The method of claim 9, wherein the inert gas is selected from the group consisting of nitrogen, carbon dioxide, argon, krypton, xenon, neon, and mixtures thereof.

11. The method of claim 8, wherein the foaming agent comprises a surfactant.

12. The method of claim 8, wherein the aqueous solution comprises an aqueous solution containing at least about 0.01 % by weight of a surfactant.

13. The method of claim 8 further comprising injecting a gas selected from the group consisting of nitrogen, carbon dioxide, argon, krypton, xenon, neon, and mixtures thereof into the sanitizing medium.

14. The method of claim 7, wherein the objects in the food processing environment comprises objects selected from the group consisting of, food surfaces, food contact surfaces, food processing equipment, food storage containers, food freezers and an ambient of the food processing environment.

15. A system for generating an ozonated foam medium comprising:

an injector having a foam solution supply and a supply of gas comprising ozone connected thereto, wherein the injector produces an aqueous stream of ozonated foam;

a foam separator coupled to the injector, wherein the foam separator receives the aqueous stream of ozonated foam and separates the ozonated foam medium from a liquid component of the aqueous stream of ozonated foam, wherein the injector and the foam separator comprise sections of an elongated pipe, and wherein the diameter of the pipe varies along a longitudinal axis thereof, such that the diameter of the foam separator section is greater than the diameter of the injector section; and a foam delivery line coupled to the foam separator and configured to receive the ozonated foam medium.

16. The system of claim 15 further comprising a solution return line connected to the foam separator and to an inlet line to the injector, wherein the recycle line receives at least a portion of the liquid component in the foam separator and sends a pressurized liquid stream to the inlet line.

17. The system of claim 16 further comprising a liquid level switch mounted to the foam separator and a control valve in the recycle line and operatively coupled to liquid level switch.

18. The system of claim 15, wherein the injector comprises a venturi tube.

19. The system of claim 15 further comprising an inert gas supply coupled to one of the injector, the supply of gas comprising ozone and both the injector and the supply of gas comprising ozone.

20. The system of claim 19 further comprising a feed gas supply coupled to the inert gas supply and to the supply of gas comprising ozone.

* * * * *